(12) United States Patent
Nakamura et al.

(10) Patent No.: US 6,426,987 B2
(45) Date of Patent: Jul. 30, 2002

(54) IMAGING SYSTEM AND METHOD OF CONSTRUCTING IMAGE USING THE SYSTEM

(75) Inventors: Hironobu Nakamura, Nishinomiya; Hiroaki Naito, Shijounawate; Seiki Hamada; Shuji Yamamoto, both of Minoo; Shogo Azemoto, Hino, all of (JP)

(73) Assignee: Kanagawa & Co., Ltd., Hyogo (JP)

( * ) Notice: Subject to any disclaimer, the term of this patent is extended or adjusted under 35 U.S.C. 154(b) by 0 days.

(21) Appl. No.: 09/801,005

(22) Filed: Mar. 8, 2001

(30) Foreign Application Priority Data

Jun. 1, 2000 (JP) ........................ 2000-163899

(51) Int. Cl.$^7$ ............................... A61B 6/03
(52) U.S. Cl. ........................... 378/4; 378/901
(58) Field of Search .............. 378/4, 15, 901

(56) References Cited

U.S. PATENT DOCUMENTS 6,154,516 A * 11/2000 Heuscher et al. ............ 378/15
2001/0048731 A1 * 12/2001 Nakamura et al. ............ 378/4

OTHER PUBLICATIONS

AJR Am J Roentgenal, Jan. 2000; 174 (1) : pp. 203–208; "Two–and Three Dimensional CT Ventriculography: A New Application of Helical CT".

* cited by examiner

Primary Examiner—David V. Bruce (57) ABSTRACT

An imaging system is provided which comprises: a CT scanner; a first storage unit storing a plurality of transverse images taken by the CT scanner; an image conversion unit producing a two-dimensional cross sectional image on the basis of the transverse images, for which the transverse images are arranged in a direction perpendicular to a transverse plane; a second storage unit storing the cross sectional image; a peak detection unit extracting an outline of the cross sectional image for detecting peaks or troughs of the outline; a peak interpolation unit carrying out interpolation on the basis of a specified standard for an outline between the peaks or between the troughs detected by the peak detecting unit; and an image construction unit reconstructing the cross sectional image stored in the second storage unit using the outline interpolated by the peak interpolation unit. The imaging system makes it possible to improve a precision and to increase a speed in peak detection when reconstructing a coronal image produced from a plurality of transverse images taken by a CT scanner.

15 Claims, 7 Drawing Sheets

IMAGING SYSTEM AND METHOD OF CONSTRUCTING IMAGE USING THE SYSTEM

CROSS-REFERENCE TO RELATED APPLICATION

This application is related to Japanese Patent Application No. 2000-163899 filed on Jun. 1, 2000, whose priority is claimed under 35 USC § 119, the disclosure of which is incorporated by reference in its entirety.

BACKGROUND OF THE INVENTION

1. Field of the Invention

The present invention relates to an imaging system in a medical field, particularly to an imaging system which can construct an image from transverse images (tomograms) taken by a CT scanner about an imaging object having a periodically changing shape like a heart.

2. Description of the Related Art

An X-ray computer tomography system (hereinafter referred to as a CT scanner) has been used for taking medical images in a medical field.

The CT scanner is a system which irradiates a diagnosing subject with X-ray to collect projection data of the X-ray transmitted through the diagnosing subject. On the basis of the projection data, an image processing is carried out to reconstruct a transverse image (also referred to as a tomogram) of visceral organs of the diagnosing subject.

Furthermore, by processing a number of the reconstructed transverse images so as to be arranged in the direction perpendicular to the transverse plane at uniform intervals to form a stack, a cross sectional image (herein after referred to as an MPR (multi-planer reconstruction) image) is reconstructed. With three-dimensional information further collected on the basis of the MPR image, production of a three-dimensional image of the diagnosing subject is also carried out.

For producing such a three-dimensional image, a large amount of the transverse images must be collected with a high speed and high precision. For this purpose, a helical type CT scanner (hereinafter referred to as a helical scanning CT) has been recently used which collects data of a helical cross sectional plane.

The helical scanning CT is used for producing a transverse image or a three-dimensional image used for examining and diagnosing a function of a heart. The image of the heart is obtained as being in a diastolic phase or systolic phase. However, a heart repeats a diastole and systole with a certain personally different characteristic period (about 60 beats/minute). Therefore, no plurality of transverse images can be obtained about the heart in the diastolic phase, for example, only at one time scanning.

Thus, in general, an electrocardiograph is provided to select the transverse images supposed to be those in the diastolic or systolic phase in synchronism with data signal obtained from the electrocardiograph. From thus selected transverse images, there are produced the MPR images or the three-dimensional images in the diastolic or systolic phase.

Figure 1:
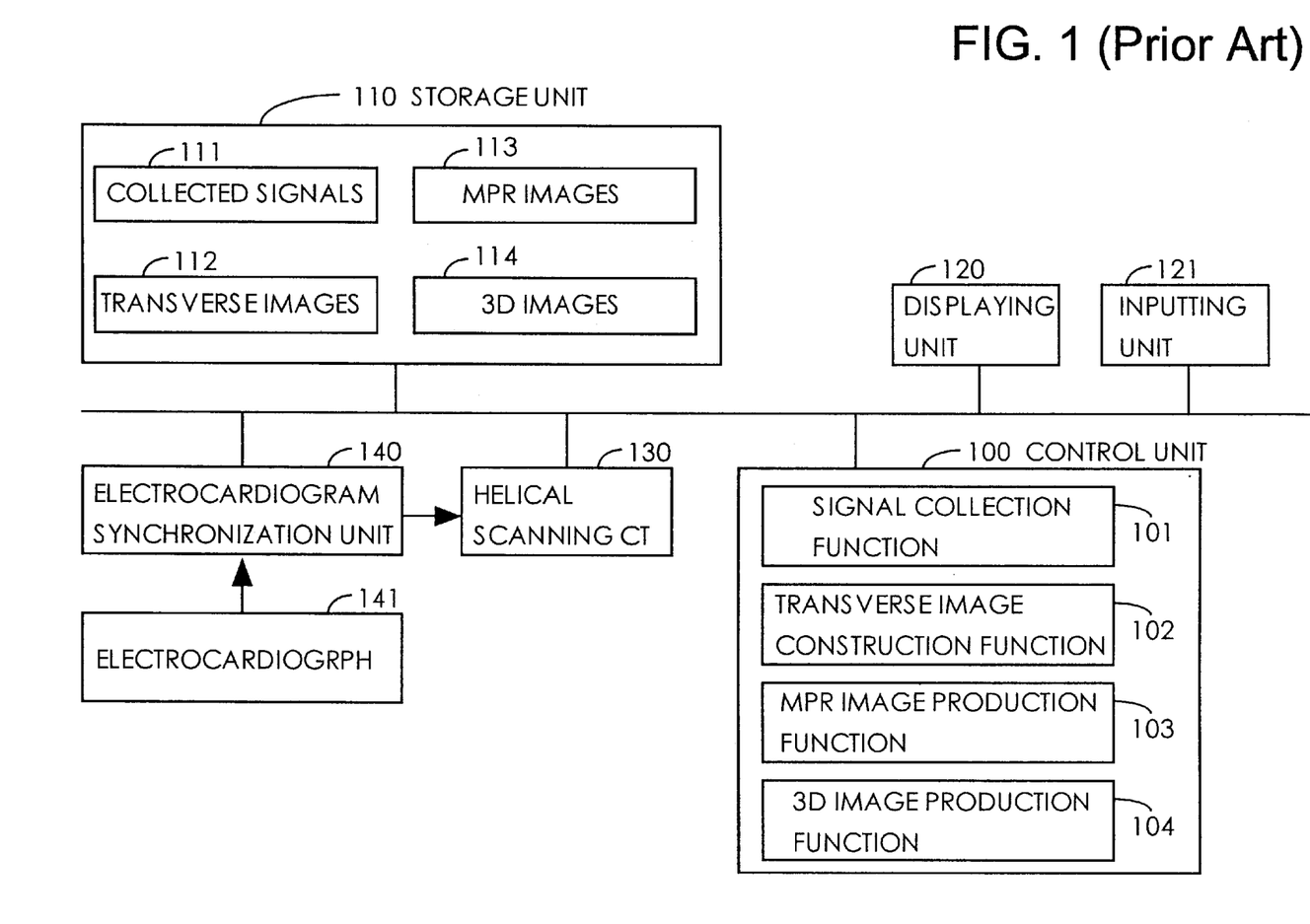
FIG. 1 is a block diagram showing an outline of a configuration of a related synchronization system of an electrocardiograph with a helical scanning CT system.

FIG. 1 is a block diagram showing an outline of a configuration of a related synchronization system of an electrocardiograph with a helical scanning CT system.

The synchronization system comprises a helical scanning CT 130, an electrocardiograph 141 outputting data of an electrocardiogram of a diagnosing subject, an electrocardiogram synchronization unit 140 analyzing electrocardiogram data of a diagnosing subject to transmit a synchronization signal to the helical scanning CT, and a computer carrying out an image processing.

In addition, the computer comprises a control unit 100 comprising a CPU and associated units, a storage unit 110, a displaying unit 120, and an inputting unit 121.

In the storage unit 110, there are stored collected signals 111, transverse images 112, MPR images 113, and three-dimensional images 114. The collected signals 111 are those of projection data obtained by the helical scanning CT, transverse images 112 are constructed from the collected signals 111, MPR images 113 are produced from the transverse images 112, and three-dimensional images 114 are produced on the basis of the MPR images 113.

The control unit 100 is provided with various functions such as a signal collection function 101, a transverse image construction function 102, an MPR image production function 103, and a three-dimensional image production function 104. The signal collection function 101 is for driving the helical scanning CT 130 and storing the collected signals 111 of the projection data in the storage unit 110. The transverse image construction function 102 is for constructing the transverse images 112 using the stored collected signals 111. The MPR image production function 103 and a three-dimensional image production function 104 are for producing the MPR images 113 and the three-dimensional images 114 using the transverse images 112 and the MPR images 113, respectively.

In such a related system used for constructing the image of a heart in a diastolic or systolic phase, data collection processing and imaging processing in the control unit 100 were generally carried out by either one of the following.

(1) Processing of driving the helical scanning CT in synchronism with a data signal of the electrocardiograph and obtaining projection data when the heart shows a little motion.

Figure 2:
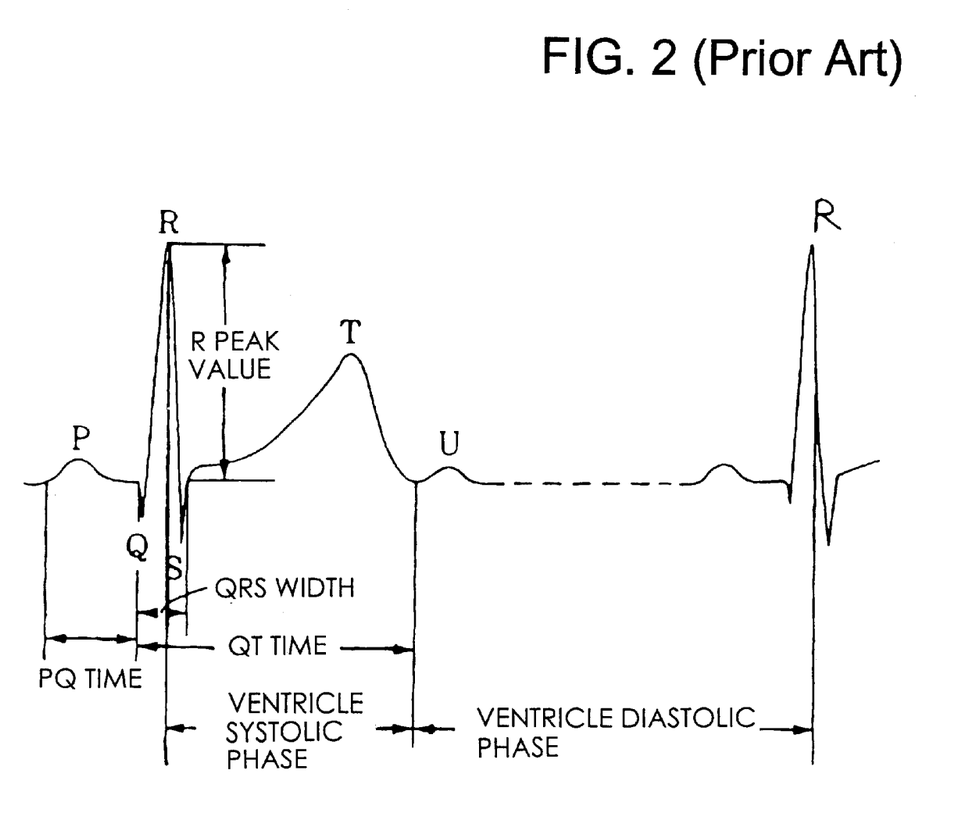
FIG. 2 is a waveform diagram showing a typical data of a cardiogram.

FIG. 2 is a waveform diagram showing a typical data signal of an electrocardiograph.

In general, in a waveform of the data signal of the electrocardiograph, it is well known that a wave form in the range between the T wave and the R wave exhibits a little variation. Here, for allowing the projection data to be obtained within the range, the electrocardiogram synchronization unit 140 transmits a trigger signal to the helical scanning CT 130 at a specified timing. The helical scanning CT 130 receiving the signal carries out a series of processing for obtaining projection data in a followed certain period.

Therefore, in the storage unit 110, only the projection data in the range with a little variation from the T wave to the R wave are stored as the collected signals 111.

After the scanning of the helical scanning CT 130 is over, the control unit 100 constructs a plurality of the transverse images 112 on the basis of the collected signals 111.

Furthermore, there is carried out processing of selecting the transverse images from a plurality of the transverse images 112 in synchronism with the data signal of the electrocardiograph. The selected transverse images 112, for example, those in a period corresponding to the systolic phase of the heart (a specified period after the T wave). On the basis of the selected images 112, processing is further carried out for producing the MPR images 113 or 3 dimensional images 114.

Also about the transverse images 112 in the diastolic phase, processing is carried out for selecting transverse images in a period corresponding to the diastolic phase (a specified period before the R wave).

(2) Processing of obtaining the projection data by the helical scanning CT without in synchronism with a data signal of the electrocardiograph, constructing transverse images on the basis of the obtained data, and selecting images corresponding to those in the diastolic or systolic phase of the heart with a measurer comparing the constructed transverse images and the waveform of the data signal of the electrocardiograph.

Here, the electrocardiogram synchronization unit 140 is not used. Namely, the control unit 100 separately stores the data signal obtained from the electrocardiograph 141 and the projection data obtained from the helical scanning CT 130 in the storage unit 110 as the collected signals 111.

After this, the control unit 100 constructs the axial CT images (transverse images) on the basis of the projection data. The constructed axial CT images include those in both the diastolic and systolic phases.

There, the axial CT images and the waveform of the data signal of the electrocardiograph are displayed on a displaying unit or printed out. From thus displayed or printed out images and waveform, images corresponding to those in the diastolic or systolic phases within the range from the T wave to the R wave are manually selected in order by the measurer with correspondence of each image with time made ascertained.

On the basis of a number of thus manually selected axial CT images, processing is carried out by the control unit 100 for producing the MPR images 113 or 3 dimensional images 114.

The helical scanning CT is a system in which linear movement of a table with a diagnosing subject mounted thereon and rotation of an X-ray tube and detectors are combined to collect the spiral projection data. The path of the X-ray always passes through a certain fixed range within the diagnosing object to provide continuous projection data in the direction of the table movement.

Namely, when transverse images with a certain thickness are constructed with the table position gradually shifted, the time at which the image is obtained becomes a little different depending on the table position. Therefore, each of the transverse images is constructed so as to include projected data obtained at times a little different from each other.

For example, when a whole heart is scanned in 37.5 sec with a helical scanning CT which has an axial resolution (slice thickness) of 2 mm, takes 0.5 sec for one rotation (scanning time =0.5 sec) and reconstructs 10 images per rotation, an image is reconstructed at 0.05 sec time intervals and 750 transverse images are obtained in total.

In general, the period of the diastole and systole of a heart of R-R 60 (60 beats/min) is about 1 sec (60 beats/60 sec). Thus, the 750 transverse images include images for the diastolic phase and those for systolic phase.

Therefore, in the case that MPR images are produced with the 750 transverse images arranged in the direction perpendicular to the transverse plane (axial plane), the MPR images is provided with a wavy outline because of mixed transverse images obtained in both the diastolic and systolic phases. Namely, although an MPR image of a heart would be obtained to have originally a smoothly varying outline when the heart was at rest, the image is obtained to have an indistinct outer shape with the outline thereof having small "peaks (maximum peaks)" and "troughs (minimum peaks). This is because the images are taken while the heart is periodically moving.

Therefore, in order to produce the MPR image in the diastolic (or systolic) phase from the transverse images, either one of the above described two kinds of processing was used to select the transverse images in the diastolic (or systolic) phase among a large number of transverse images.

Both of the two kinds of processing, however, requires the measurer to work for visually ascertaining a large number of transverse images and data of electrocardiogram, for which a long period of several days was necessary.

In particular, in the above processing (1), the electrocardiogram synchronization unit 140 was necessary for the synchronization with the data signal of the electrocardiograph, which further required complicated preprocessing for the synchronization including adjustment and parameter setting of the units shown in FIG. 1.

In the processing (2), the work for selecting transverse images required the measurer to have a high expert knowledge and to spend a lot of time. Furthermore, the work of selection was carried out subjectively without flexible applicability.

SUMMARY OF THE INVENTION

Accordingly, it is an object of the present invention to provide an imaging system which can construct sharp images with a high speed, high precision and easiness without requiring any electrocardiogram synchronization unit and any image selection processing by a measurer having expert knowledge, even for an imaging object moving periodically such as a heart.

The above object can be accomplished by an imaging system which comprises a CT scanner; a first storage unit storing a plurality of transverse images taken by the CT scanner; an image conversion unit producing a two-dimensional cross sectional image on the basis of the transverse images, for which the transverse images are arranged in a direction perpendicular to a transverse plane; a second storage unit storing the cross sectional image; a peak detection unit extracting an outline of the cross sectional image for detecting peaks or troughs of the outline; a peak interpolation unit carrying out interpolation on the basis of a specified standard for an outline between the peaks or between the troughs detected by the peak detecting unit; and an image reconstruction unit of the cross sectional image stored in the second storage unit using the outline interpolated by the peak interpolation unit.

With the system, the cross sectional image of the diagnosing subject can be constructed with higher speed, higher precision, and more easiness.

In addition, according to the present invention, when an imaging object of the CT scanner is a heart, the image conversion unit produces a cross sectional image of the heart; thereafter, the peak detection unit detects peaks; the peak interpolation unit carries out interpolation for an outline between the detected peaks; and the image reconstruction unit reconstructs the cross sectional image of the heart in the diastolic phase by using the interpolated outline.

Similarly, by using the detected troughs, the cross sectional image of the heart in the systolic phase can be reconstructed.

It is also possible for the system to detect the peaks or troughs with nonuniform intervals. This makes it possible to produce the cross sectional image of the heart in the diastolic or systolic phase with a high speed, high precision, and easiness without visual ascertaining work of the measurer.

In the present invention, the cross sectional image means a so-called MPR (Multi Planar Reconstruction) image. Therefore, the MPR image includes tomograms in all directions which are reconstructed from the projection data obtained by the CT scanner. In the present invention, however, coronal images or sagittal images are to be mainly reconstructed as the MPR images. Particularly in the following embodiments, the coronal image is explained as the MPR image. However, the present invention is not limited to this, but can be applied all kinds of cross sectional images.

In the present invention, the CT scanner may be of any type of scanning method used in the medical field such as T/R method, R/R method, S/R method, N/R method, and helical scanning method. However, since the imaging object of the present invention is a diagnosing subject with a periodical movement, a high speed and high precision CT scanner is required. Thus, it is preferable to use the helical scanning type CT scanner which can finish image-taking of whole diagnosing subject with a high precision while the subject is holding breath.

For the first storage unit and second storage unit, a rewritable storage unit of a semiconductor device (RAM) or a hard disk can be used. In the present invention, a remarkable amount of storage capacity is necessary for both the transverse images stored in the first storage unit and the cross sectional images (MPR images) stored in the second storage unit. Thus, it is preferable to use a mass storage and quick access type storage device such as a hard disk or a magneto-optical disk.

The image conversion unit according to the present invention comprises a control program executing MPR images producing function. Specifically, the unit is a section in which a microcomputer with a CPU executes a specified algorithmic operation on the basis of the control program to thereby output the cross sectional images.

The peak detection unit according to the present invention comprises a control program executing a so-called peak detection function which extracts the outline of the cross sectional image and detects the peaks or troughs of the outline.

The control program is executed with the data of the cross sectional image inputted and data of the positions of the peaks or those of the troughs outputted.

An algorithm for detecting positions of the peaks and the troughs is realized by a difference operation (See "Kagakukeisoku no tame no Hakei Data Shori (Waveform Data Processing in Scientific Measurement)", ed. by Shigeo Minami, CQ Publication Co., Ltd., Apr. 30, 1986 (in Japanese)).

The peak interpolation unit according to the present invention comprises a control program executing a function (peak interpolation function) of interpolating between the obtained two peaks (or two troughs). The control program is executed with the peaks and the toughs inputted and an interpolated value between the peaks outputted.

For example, interpolation algorithm is realized by linear interpolation method (See Yasuzo Sudou, "Igaku ni okeru Sanjigen Gazoshori (Three Dimensional Image Processing in Medical Science)", CORONA PUBLISHING CO., LTD., Mar. 10, 1995 (in Japanese)).

The image construction unit according to the present invention comprises a control program executing a function of reconstructing cross sectional images, in which approximately the same algorithm as that used for the image conversion unit can be used. The control program is executed with transverse images corresponding to the interpolated outline inputted and the cross sectional images outputted.

The image conversion unit, peak detection unit, peak interpolation unit, and image construction unit can be realized by single control unit as will be explained later, for example, a personal computer or workstation.

The control program realizing the above described functions can be stored in a fixed storage medium such as a hard disk. In addition to this, the program can be stored in a portable storage medium such as a CD-ROM, MO, or DVD-ROM. Alternatively, the control program can be also stored in a server for being transferred to a personal computer at a remote location through a network.

DESCRIPTION OF THE PREFERRED EMBODIMENTS

The present invention will be explained in detail on the basis of embodiments. However, the present invention is not limited to the embodiments.

Figure 3:
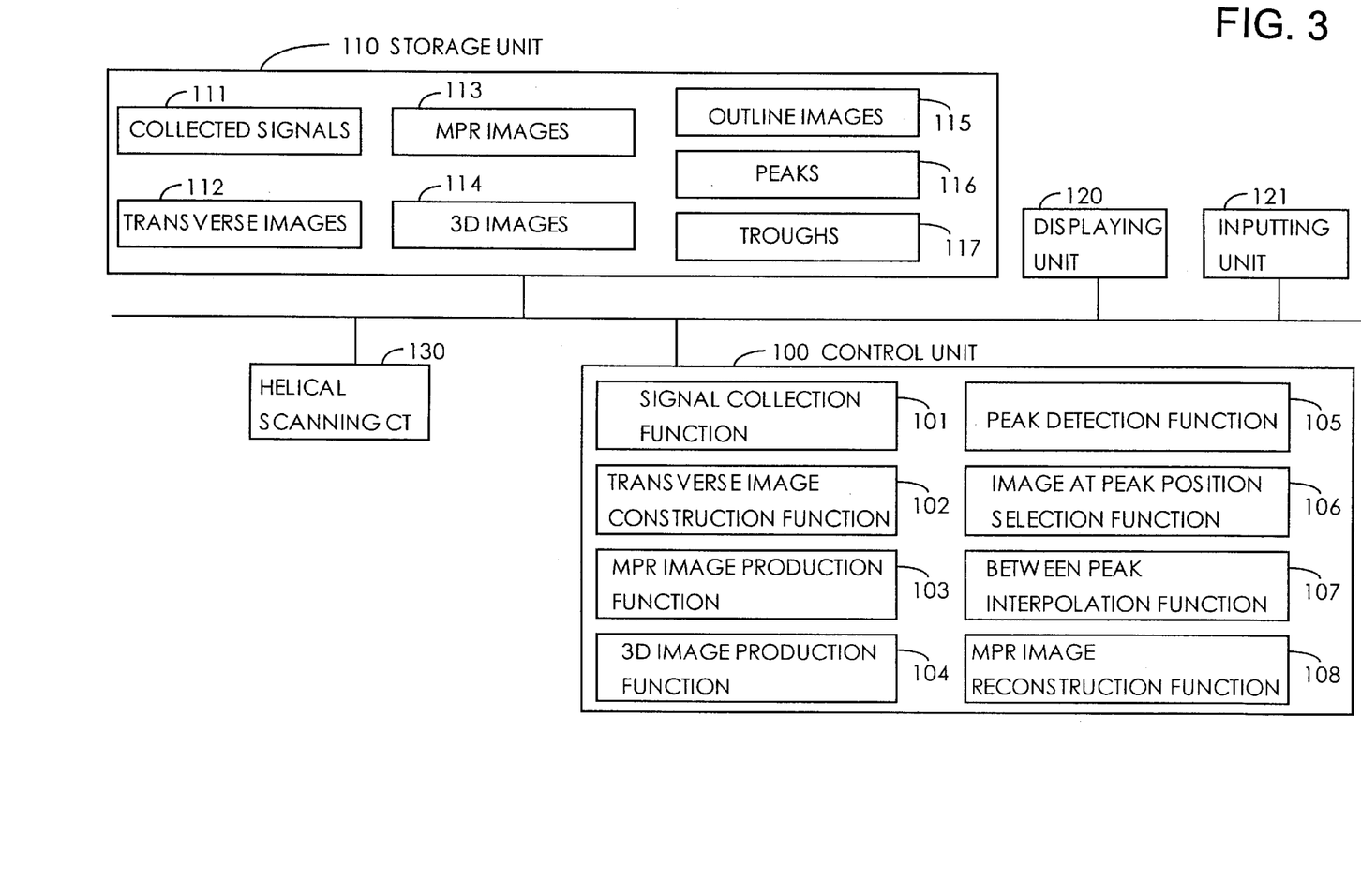
FIG. 3 is a block diagram showing an embodiment of an imaging system according to the present invention.

FIG. 3 is a block diagram showing an embodiment of an imaging system according to the present invention.

The system of the embodiment can be applied to a periodically moving diagnosing subject, and construction of an image of a heart in the diastolic and systolic phases will be explained below.

The system according to the present invention, compared with the related system shown in FIG. 1, is different from the related one in that it necessitates no electrocardiogram synchronization unit 140 and no electrocardiograph 141.

In FIG. 3, a helical scanning CT 130 may be one which has been conventionally used. However, for constructing an image with a high resolution, one with an X-ray tube rotated at a high speed and detectors with high resolution is preferable.

For example, a helical scanning CT with a performance of a rotation speed of 2 rps and a slice thickness (resolution) of about 0.5 mm can be used ("Aquilion" supplied from Toshiba Corp.).

For a control unit 100, a so-called personal computer or workstation can be used. Namely, a microcomputer can be used which comprises ROM, RAM, various I/O interfaces, a timer, and associated peripheral equipment with CPU centered. In addition, control programs for realizing various functions according to the present invention are stored in storage media in the control unit 100 such as semiconductor storage devices such as ROM and RAM, or a hard disk.

A storage unit 110 is for storing the control programs and, in addition thereto, obtained collected signals, data of constructed images, setting parameters and intermediate status data while various functions are being executed. For the unit 110, various storage media can be used such as rewritable semiconductor memories (RAM), hard disks (HD), MO, MD, PD, DVD-RAM.

In the storage unit 110 according to the present invention, there are stored, for example, collected signals 111 obtained from the helical scanning CT 130, transverse images 112 constructed from the collected signals 111, coronal images (MPR images) 113 produced on the basis of the transverse images 112, three-dimensional images 114 of the diagnosing subject, outline images 115 of extracted outlines of the MPR images 113, and positional data of peaks 116 and troughs 117 of the outlines of the outline images 115.

A displaying unit 120 is for displaying the transverse images, MPR images, and three dimensional images constructed by imaging processing, for which various kinds of displaying units such as CRT, LCD, and PDP can be used depending on applications.

An inputting unit 121 is for operation of inputting setting parameters, inputting indication of various operations, starting and stopping of various functions. For the inputting unit 121, in addition to a keyboard, various pointing devices such as a mouse and a track ball can be used.

Details of processing carried out in the control unit 100 will be explained in the following.

Figure 4:
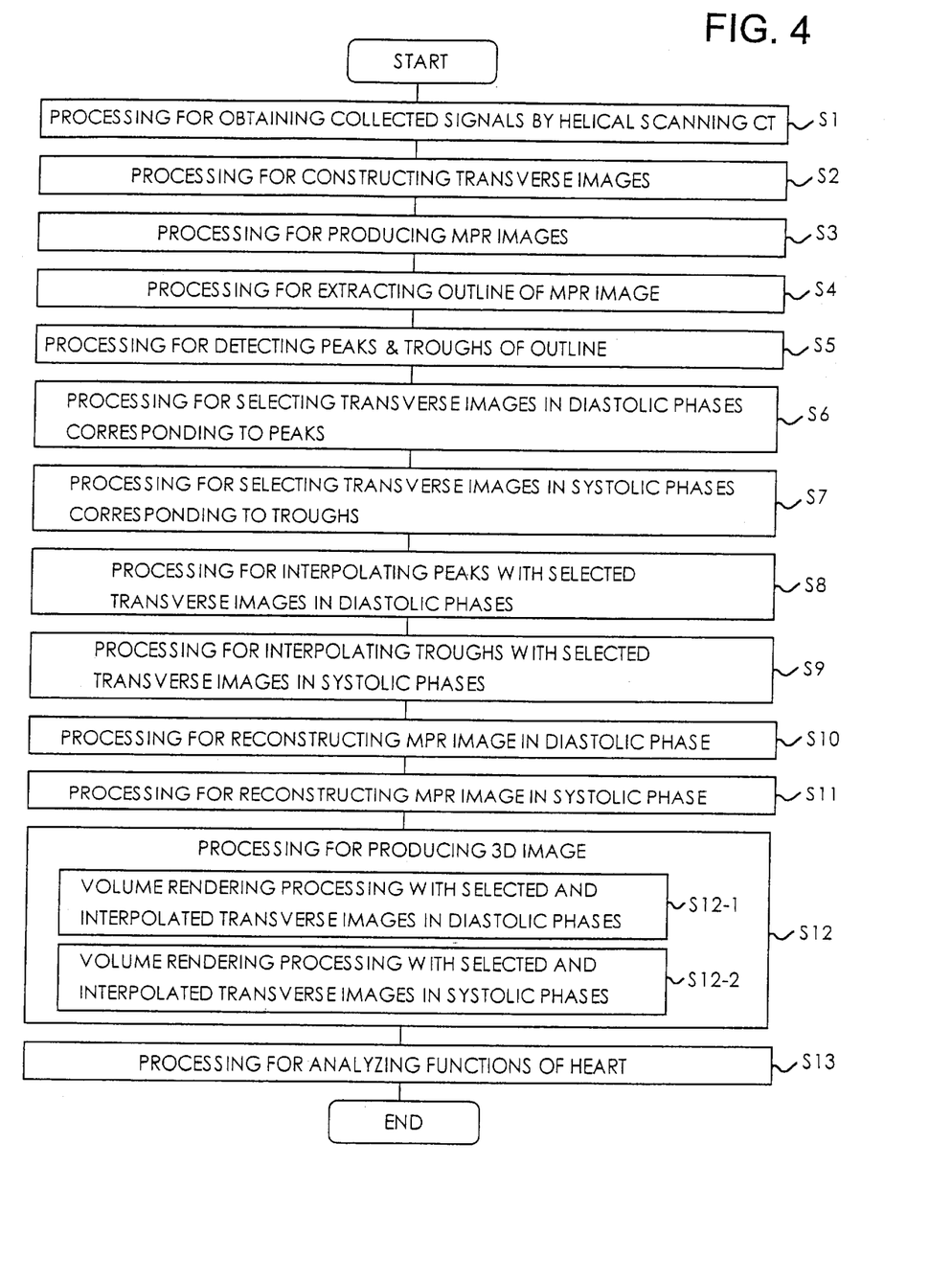
FIG. 4 is a flowchart showing whole processing carried out in a control unit in the imaging system according to the present invention.

FIG. 4 is a flowchart showing whole processing carried out in the control unit 100 according to the present invention.

The processing carried out in the control unit 100 comprises those mainly carried out by eight function blocks shown in FIG. 3.

Here, a signal collection function block 101 is a part carrying out processing for obtaining the collected signals 111 by the helical scanning CT 130 (step S1 in FIG. 4). A transverse image construction function block 102 is a part carrying out processing for constructing the transverse images 112 by using the obtained collected signals 111 (step S2 in FIG. 4). An MPR image production function block 103 is a part carrying out processing for producing the MPR images 113 by using the constructed transverse images 112 (step S3 in FIG. 4). A three-dimensional image production function block 104 is a part carrying out processing for producing the three-dimensional images 114 of the diagnosing subject (a heart, for example) from the obtained MPR images 113 (step S12 in FIG. 4).

The four function blocks can be processed by using the same processing as that realized in the related imaging system shown in FIG. 1.

In FIG. 3, four function blocks of a peak detection function 105, an image at peak position selection function 106, a between peaks interpolation function 107, and an MPR images reconstruction function 108 are those characteristic to the system according to the present invention.

The peak detection function block 105 is a part carrying out processing for extracting an outline of an MPR image 113 obtained by the MPR image production function block 103, producing the outline image 115, and detecting tops and bottoms of the edge of the outline image 115, namely, peaks and troughs.

Here, for the processing for extracting the outline, various methods can be used such as an automatic tracing used in computer graphics for drawing an outline.

Also for the processing for detecting peaks, various methods can be used. Typical one of such is a method in which slopes of the waveform of a signal are successively obtained to find the peaks and the troughs by the difference operation. Another is a smoothing differentiation method in which a smoothing processing of the extracted outline is carried out with a moving-average method or a frequency region method before being processed by the difference operation.

By the peak detection function 105, data are obtained about positions of a number of the peaks and the troughs on the edge of the targeted outline image.

Instead of the peak position detection with the specified automatic processing programmed in the control unit as above, the detection of the peaks and the troughs may be carried out as follows. In the detection, the obtained MPR image 113 is displayed on the displaying unit 120, with the outline part enlarged in some cases, and the positions of the tops and bottoms on the edge of the outline are inputted by indication of the measurer.

The indicated positions of the peaks can be more easily inputted with the use of a pointing device such as a mouse.

The image at peak position selection function 106 is a part carrying out processing for selecting transverse images 112 corresponding to those at a number of positions of, for example, the peaks.

Interpolation between two peaks is carried out with the transverse images at the peak positions used by the between peaks interpolation function 107 that will be described later. This provides a reconstructed MPR image constructed only with the transverse images corresponding to those in the so-called diastolic phase.

The processing for selecting the transverse images 112 can be carried out by selecting from the storage unit 110 the transverse images 112 which are made in correspondence in time to the positions of the peaks or the troughs. That is, the selection can be made by carrying out some kind of flagging indicating selection of the above transverse images 112 in the diastolic (or systolic) phase.

The between peaks interpolation function 107 is a part carrying out processing for estimating positions of edges between two selected peaks and producing transverse images equivalent to those to be between the transverse images at the positions of the above two peaks (referred to as an interpolated image).

For interpolation between peaks, in addition to the so-called "linear interpolation method", the "nonlinear interpolation method" can be used. In the "linear interpolation method", a linear interpolation is carried out with a ratio of the distance of the interpolated image from one of the peak to the distance between the two peaks. In the "nonlinear interpolation method", the images are once converted into images called as distance images before being processed by general interpolation processing such as linear interpolation.

The MPR images reconstruction function 108 is a part carrying out reconstruction of the MPR image 113 by using the transverse images at the position of the peaks and the interpolated images produced by the between peaks interpolation function 107. This can be carried out by the same processing as that of the MPR image production function 103 only with difference in used transverse images.

With such processing, MPR images can be produced as corresponding to those in the diastolic or systolic phases of a heart.

Each of the above functions can be realized by the control unit 100 executing control programs in a specified order.

An example of processing carried out by the control unit in the embodiment of the imaging system according to the present invention will be explained on the basis of the flowchart shown in FIG. 4.

Here, a heart of a human body is taken as a diagnosing subject.

First, the projection data of the diagnosing subject are collected by the helical scanning CT 130 and the collected signals 111 of the projection data are stored in the storage unit 110 (step S1).

Here, a present helical scanning CT 130 can be used with a performance of a rotation speed of 2 rpm, axial resolution (slice thickness) of 0.5 mm, spatial resolution of 0.5 mm, and gray level value (CT value) indication with 16 bit code.

Let the length of the heart in the axial direction be 70 mm, for example. If we let the helical scanning CT 130 be moved by 2.5 mm per one rotation, the rotation speed of taking 0.5 sec per rotation provides a moving speed of 2.5 mm/0.5 sec =5 mm/sec. Here, the moving distance per one rotation to the slice thickness is called as a helical pitch. The above moving distance per rotation of 2.5 mm is equivalent to five times the slice thickness (0.5 mm). Thus, the helical pitch in the above case is called as a helical pitch 1:5 or a helical pitch 5. Therefore, for the helical pitch 5, a scanning of the whole heart (70 mm in length) takes 70/5=14 sec.

This shows that the scanning of the whole heart can be completed in a comparatively short time of the order of 14 sec.

Following this, on the basis of the collected signals 111, the transverse images are constructed by the normally carried out image processing (step S2). For example, the whole heart (70 mm in length) is constructed with the transverse images 112 of the number of 70 mm/0.5 mm =140.

As described above, the scanning time for the whole heart is 14 sec. While, the period of the beat of a heart is generally about 1 sec. Therefore the constructed transverse images 112 mixedly include those in the diastolic phases of the heart and those in the systolic phases.

Figure 5:
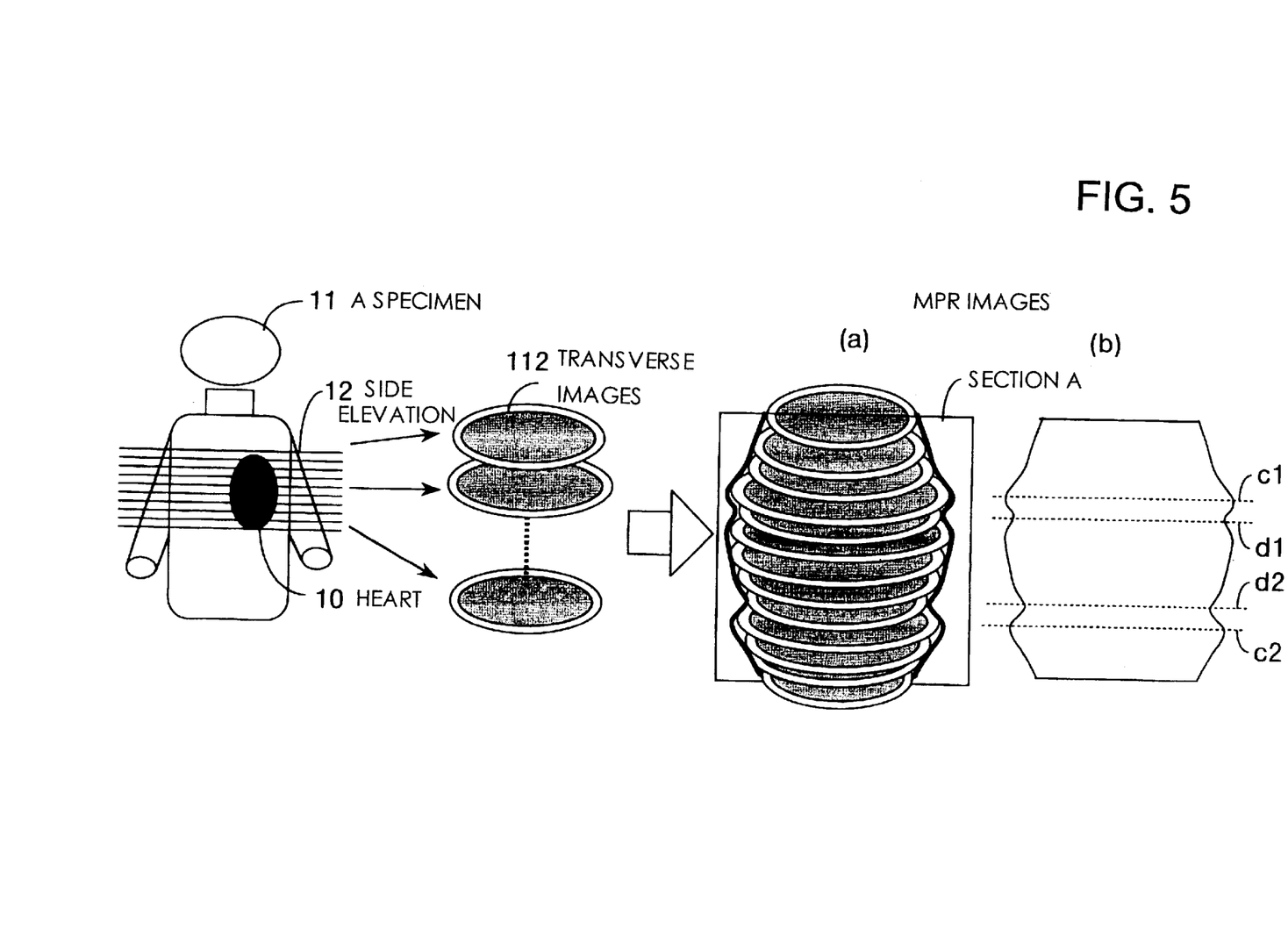
FIG. 5 is a schematic illustration showing a flow of constructing an MPR image.

FIG. 5 is a schematic illustration showing a flow of constructing an MPR image.

The transverse images 112 are obtained as axial images for which a heart 10 of a diagnosing subject 11 is cut transversally along transverse planes 12 as shown in the figure.

Returning to FIG. 4, as a next step, processing for producing an MPR image is carried out (step S3).

With reference to FIG. 5, the MPR image 113 is a coronal image on a two-dimensional cross sectional plane A. For the image, all of the transverse images 112 obtained in step S2 are arranged in the direction perpendicular to the transverse planes 12 to be cut along a plane perpendicular to the transverse planes 12.

Since the MPR image 113 is produced on the basis of the transverse images mixed with those in the diastolic and systolic phases, the outline thereof is made to have minute irregularity.

For example, in the MPR image 113 in FIG. 5, the outline has "tops" at line segments c1 and c2. This shows that the portions are constructed on the basis of the transverse images 112 in the diastolic phase.

Furthermore, the outline has "bottoms" at line segments d1 and d2. This shows that the portions are constructed on the basis of the transverse images 112 in the systolic phase.

Next, processing for extracting the outline of the MPR image 113 is carried out (step S4).

To the extraction processing, there can be applied the processing that is normally carried out with an application software for image processing.

With the extraction processing, an outline image 115 having only an outline is produced as shown in FIG. 5.

Following this, there is carried out processing for detecting peaks and troughs of the outline image 115 (step S5).

The processing for the detection can be carried out by the difference operation as described before. The positions of the detected peaks 116 and troughs 117 are stored in the storage unit 110.

Figure 6:
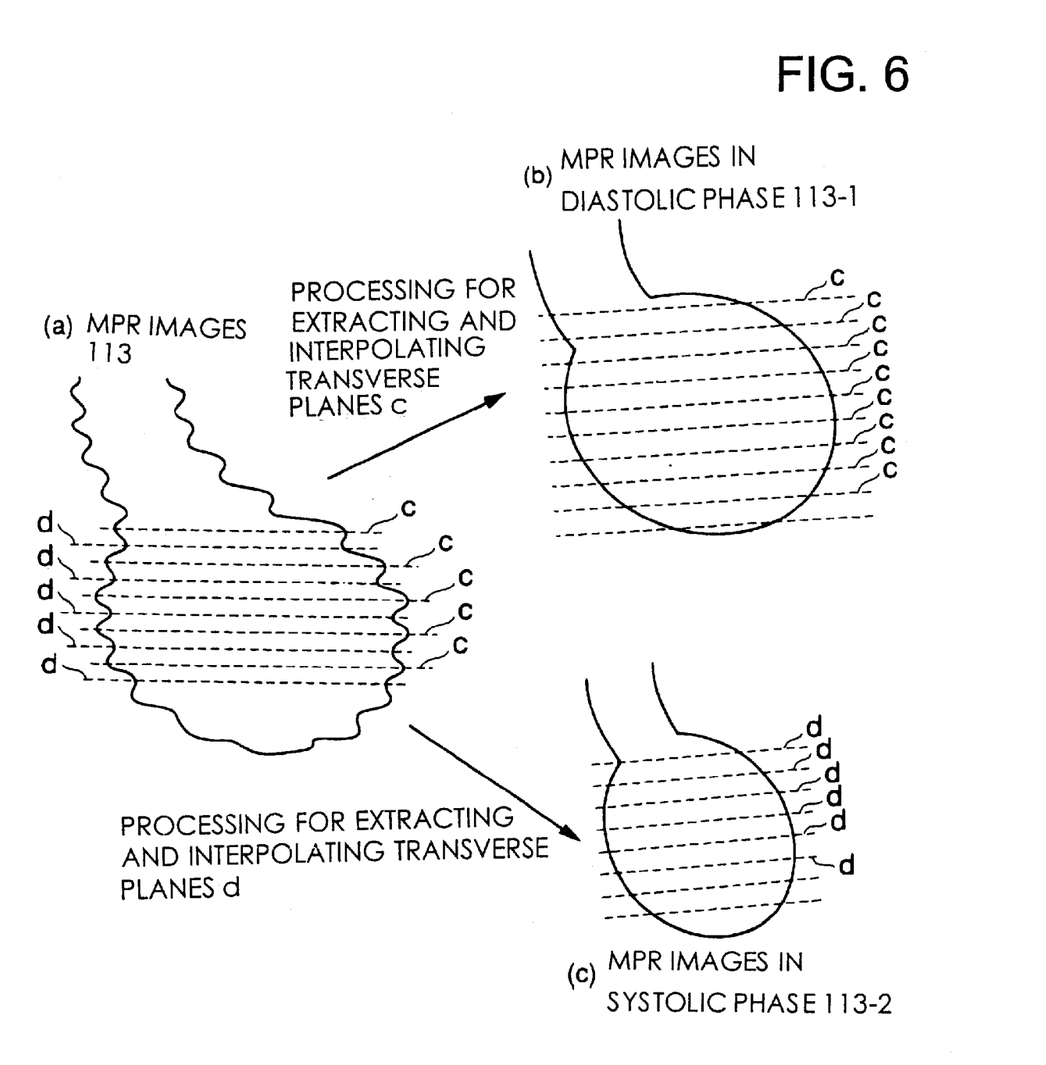
FIG. 6 is a schematic diagram showing MPR images of a heart produced by the processing according to the present invention.

FIG. 6 is a schematic diagram showing MPR images of a heart produced by the processing according to the present invention.

The outline image 115 of the MPR image 113 extracted at step S4 has tops and bottoms as shown in FIG. 6. With the extraction processing in step S5, positions shown with transverse planes c are detected as those of tops (peaks), while positions shown by transverse planes d are as those of bottoms (troughs).

Here, even for nonuniform intervals between the positions of the transverse planes c and d, the positions can be detected easily and surely.

The transverse images corresponding to the respective transverse planes c or d can be easily selected by retrieving the transverse images 112 stored in the storage unit 110.

In step S6, processing is carried out for selecting from the storage unit 110 transverse images in the diastolic phase corresponding to the positions of the obtained peaks (transverse planes c).

For example, for a helical pitch of 3 (the moving distance for one rotation becomes three times the slice thickness of 0.5 mm, i.e. 0.5×3 =1.5 mm), the moving distance in one second becomes 3 mm. For a heart of a human body with 60 beats/ min, the period between diastoles is one second. Thus, images in the diastolic phase can be selected with 3 mm intervals. The 3 mm interval includes 6 images with 0.5 mm slice thickness. Thus, of the 140 transverse images constructed in step S4, there are selected the order of 140/6=23 transverse images in the diastolic phases.

Furthermore, in step S7, processing is carried out for selecting from the storage unit 110 transverse images in the systolic phase corresponding to the positions of the obtained troughs (transverse planes d).

Next to this, in step S8, processing is carried out for interpolating the peaks.

With the 23 transverse images in the diastolic phases selected in step S6, an MPR image in the diastolic phase is reconstructed. However, since transverse images between the two transverse images in the diastolic phase are thinned out, processing for interpolating between the peaks is carried out for interpolating the thinned out transverse images as will be described later. For the interpolation processing, the previously described linear or nonlinear interpolation processing can be used.

For example, in FIG. 6, instead of the trough at a position d between positions of two transverse planes c (peaks), a point, an intersection point of a straight line connecting the two peaks, is taken as an interpolation point of the outline.

Then, processing is carried out for producing a transverse image corresponding to the above interpolation point from the two transverse images in the diastolic phases corresponding to positions of the two peaks, respectively.

Following this, in step S9, processing is carried out for interpolating the troughs. The processing is carried out in the same way as that for interpolating the peaks in step S8 with only difference therefrom being use of troughs instead of the peaks.

Thus, there are formed transverse images in the systolic phase between the troughs.

Next, in step S10, an MPR image is reconstructed by using the transverse images in the diastolic phases selected in step S6 and those produced in step S8. The reconstruction processing is carried out in the same way as carried out in step S3. The reconstruction processing provides an MPR image in the diastolic phase 113-1 as shown in FIG. 6.

Further, reconstruction of an MPR image using the transverse images in the systolic phases selected in step S7 and those produced in step S9 (step S11) provides an MPR image in the diastolic phase 113-2 as shown in FIG. 6.

With the processing as described above, from an indistinct MPR image with a wavy outline due to mixed images in both the diastolic and systolic phases, an MPR image corresponding to the diastolic phase and an MPR image corresponding to the systolic phase could be separately obtained.

By using the MPR images obtained in steps S10 and S11, precision of image extraction can be ascertained about the diastolic phase and systolic phase of the heart.

All of the processing from step S2 to step S11 can be carried out by single control unit 100. Furthermore, this can be executed within a short time of several minutes until the MPR images 113-1 and 113-2 are reconstructed after the collected signals 111 from the helical scanning CT are stored in the storage unit 110.

As a next step, three-dimensional images in the diastolic and systolic phases are produced with the transverse images obtained in the processing from step S6 to step S9 (step S12).

The three-dimensional image can be produced by well-known technique for which such a method as the volume rendering method, geometric model method, or voxel method can be employed.

Namely, a three-dimensional image in the diastolic phase is produced by, for example, the volume rendering processing with the transverse images selected in step S6 and those produced by interpolation processing in step S8 (step S12-1). The transverse images selected in step S6 are those in the diastolic phases at the positions of the peaks, and those produced in step S8 also correspond to the diastolic phase. In the same way, a three-dimensional image in the systolic phase is produced by, for example, the volume rendering processing with the transverse images selected in step S7 and those produced by interpolation processing in step S9 (step S12-2). The transverse images selected in step S7 are those in the systolic phases at the positions of the troughs, and those produced in step S9 also correspond to the systolic phase.

For producing the three-dimensional image, it is preferable for the axial resolution of the CT scanner to be less than about 0.7 mm, for which isotropic voxels are formed each having equal spatial resolution and axial resolution.

The MPR images obtained in steps S10 and S 11 are sharp ones each having a sharp outline without irregularity. Thus, each of the three-dimensional images obtained in step S12 also has a sharp outer shape.

Following this, in step S13, processing for analyzing various functions of a heart is carried out as follows.

The analyses are, for example:
1) processing for calculating out the volume of a heart in a diastolic phase from the three-dimensional image in the diastolic phase;
2) processing for calculating out the volume of a heart in a systolic phase from the three-dimensional image in the systolic phase;
3) processing for producing a moving image of a heart repeating diastole and systole from a plurality of three-dimensional images; and
4) processing for detecting abnormal portions on the surface of a heart from three-dimensional images.

Any of the above processing can be carried out by combining control programs realized at present.

Here, the images obtained in steps S10 to S12, being more sharply provided than previous ones, can improve accuracy of various kinds of analyses carried out in step S13.

In the processing in step S5 in FIG. 4, the peaks and the troughs can be detected even they are positioned at nonuniform intervals. The peaks, however, may be also detected by selection of a measurer who actually carries out visual observation of the peaks and troughs of the outline of an MPR image produced in step S3. At this time, the MPR image is displayed on the display unit 120 with the outline partially enlarged.

The operation for the selection can be carried out by using various kinds of inputting units 121 such as a mouse.

In this way, with a manual operation allowed to be carried out by a measurer, an image of a local part in the diastolic or systolic phases can be easily obtained as desired by the measurer.

Figure 7:
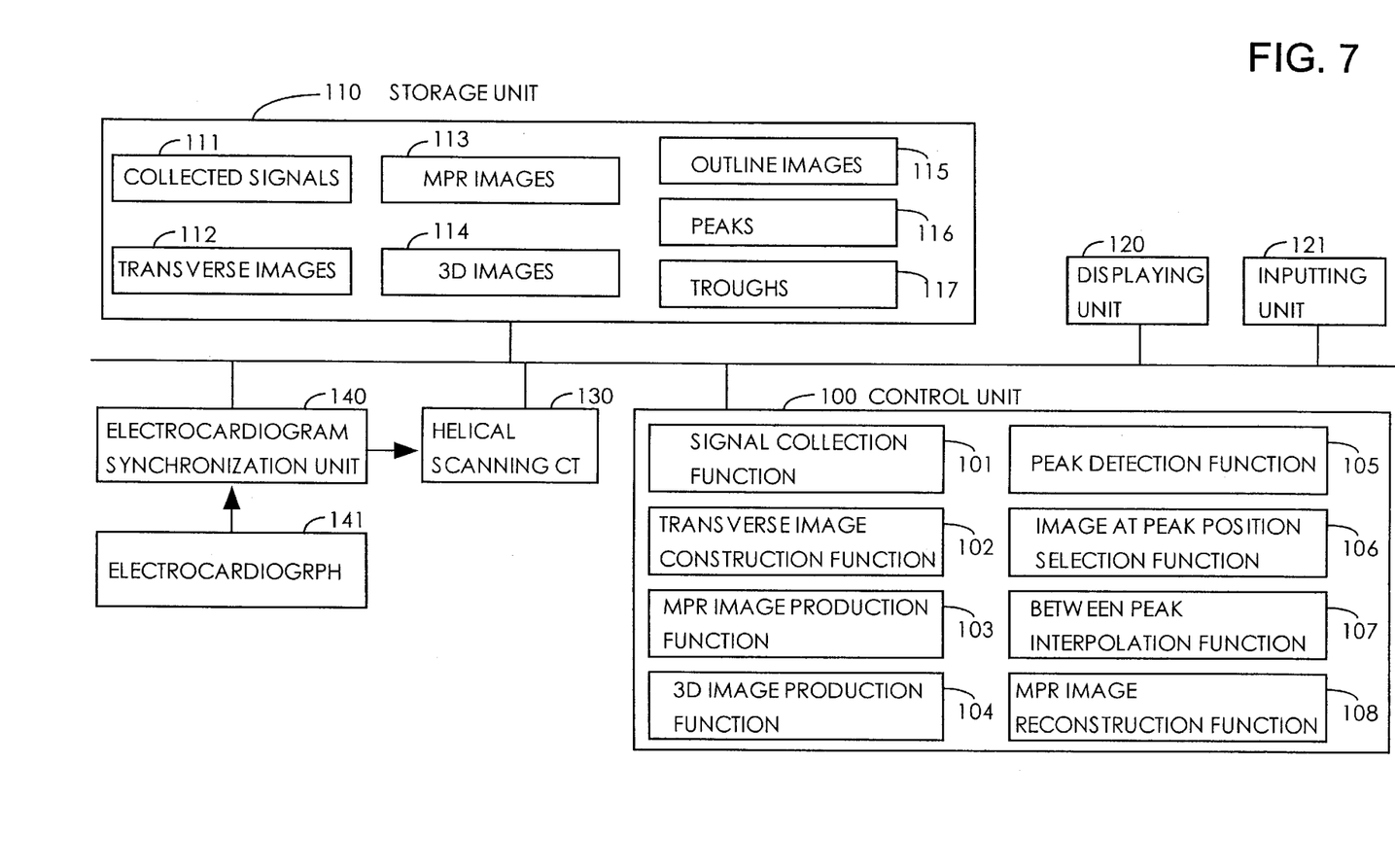
FIG. 7 is a block diagram showing another embodiment of an imaging system according to the present invention.

Also in the present invention, as shown in FIG. 3, it is not always necessary for the system to be in synchronism with a signal of an electrocardiogram. However, for more improved precision, an electrocardiograph 141 and electrocardiogram synchronization unit 140 may be added as shown in FIG. 7 so as to drive the helical scanning CT in synchronism with the electrocardiogram like in a related system.

In the present invention, in step S1 the inputted image signals of the diagnosing subject are those obtained by the helical scanning CT. In addition to this, the image signals may be those obtained by MRI (Magnetic Resonance Imaging) system or PET (Positron Emission Tomography).

In the embodiments, a heart was explained as the diagnosing subject. However, the present invention can be also applied to other visceral organs exhibiting periodical movement (such as lungs).

According to the present invention, even for a periodically moving imaging object such as a heart, a sharp coronal image and three dimensional image can be constructed from images obtained by a helical scanning CT with a high speed, high precision and easiness.

In addition, when obtaining images with the helical scanning CT, no unit is necessary for synchronization with an electrocardiograph and no image selection is also necessary which is processed by a measurer having expert knowledge.

Furthermore, when a heart is examined with the helical scanning CT, no special device is necessary to be attached to the examinee. Moreover, it takes only 20 to 30 sec for scanning the whole heart, so that the examination can be completed only by forcing the examinee to hold breath one time. This can reduce an amount of X-ray irradiation compared with an examination with the related system that necessitates synchronization with an electrocardiograph. Therefore, the examination can be made noninvasive and remarkably time saving to make it possible to construct an examination system causing no pain to patients.

In addition, after the signals of the projection data are collected by the helical scanning CT, a series of processing, from the construction of the transverse image to the analyses of the function of the heart, can be carried out by single control unit without any intervention of manual operation. Thus, the series of operations can be easily carried out without requiring any special knowledge of image processing.

What is claimed is:

1. An imaging system comprising:

a CT scanner;

a first storage unit storing a plurality of transverse images taken by the CT scanner;

an image conversion unit producing a two-dimensional cross sectional image on the basis of the transverse images, for which the transverse images are arranged in a direction perpendicular to a transverse plane;

a second storage unit storing the cross sectional image;

a peak detection unit extracting an outline of the cross sectional image for detecting relative extreme peaks of the outline;

a peak interpolation unit carrying out interpolation on the basis of a specified standard for an outline between the relative extreme peaks detected by the peak detecting unit; and an image construction unit reconstructing the cross sectional image stored in the second storage unit using the outline interpolated by the peak interpolation unit.

2. An imaging system as claimed in claim 1 further comprising a three-dimensional image production unit producing a three-dimensional image using a plurality of the cross sectional images reconstructed by the image construction unit.

3. An imaging system as claimed in claim 2 further comprising an outputting unit outputting the three-dimensional image.

4. An imaging system as claimed in claim 1 further comprising:

an image displaying unit displaying at least the cross sectional image; and a selection unit provided in the peak detection unit for allowing a user to select the relative extreme peaks of the outline of the cross sectional image displayed on the image displaying unit while the user observing the cross sectional image.

5. An imaging system as claimed in claim 1 wherein the peak detection unit detects the relative extreme peaks by smoothing differentiation processing.

6. An imaging system as claimed in claim 1 wherein the CT scanner is provided with an image pick-up unit rotating around an imaging object, the image pick-up unit rotating with a rotating speed of two rotations per minute at least.

7. An imaging system as claimed in claim 1 wherein the relative extreme peaks are peaks.

8. An imaging system as claimed in claim 1 wherein the relative extreme peaks are troughs.

9. A method of constructing an image of a heart using the imaging system as claimed in claim 1 comprising the steps of:

when an imaging object of the CT scanner is a heart, producing a cross sectional image of the heart with the image conversion unit;

thereafter, detecting peaks with the peak detection unit;

carrying out interpolation for an outline between the detected peaks with the peak interpolation unit; and reconstructing the cross sectional image of the heart in a diastolic phase with the image construction unit using the interpolated outline.

10. A method of constructing an image of a heart using the imaging system as claimed in claim 1 comprising the steps of:

when an imaging object of the CT scanner is a heart, producing a cross sectional image of the heart with the image conversion unit;

thereafter, detecting troughs with the peak detection unit;

carrying out interpolation for an outline between the detected troughs with the peak interpolation unit; and reconstructing the cross sectional image of the heart in a systolic phase with the image construction unit using the interpolated outline.

11. A storage medium stored with an image construction program, the program comprising:

an image conversion function for converting transverse images picked up by a CT scanner into a two-dimensional cross sectional image for which the transverse images are arranged in a direction perpendicular to a transverse plane;

a peak detection function extracting an outline of the cross sectional image for detecting relative extreme peaks; and a peak interpolation function for carrying out interpolation on the basis of a specified standard for an outline between the relative extreme peaks.

12. A storage medium stored with an image construction program as claimed in claim 11 wherein the relative extreme peaks are peaks.

13. A storage medium stored with an image construction program as claimed in claim 11 wherein the relative extreme peaks are troughs.

14. A storage medium stored with an image construction program as claimed in claim 11 wherein the program further comprises:

an image construction function for reconstructing the cross sectional image by using the outline interpolated by the peak interpolation function; and a three-dimensional image production function for producing a three-dimensional image from a plurality of the cross sectional images reconstructed by the image construction function, and when an object of image pick-up of the CT scanner is a heart, producing the three-dimensional image of the heart in a diastolic phase from the cross sectional images reconstructed by carrying out interpolation for an outline between the detected peaks.

15. A storage medium stored with an image construction program as claimed in claim 11 wherein the program further comprises:

an image construction function for reconstructing the cross sectional image by using the outline interpolated by the peak interpolation function; and a three-dimensional image production function for producing a three-dimensional image from a plurality of the cross sectional images reconstructed by the image construction function, and when an object of image pick-up of the CT scanner is a heart, producing the three-dimensional image of the heart in a systolic phase from the cross sectional images reconstructed by carrying out interpolation for an outline between the detected troughs.

* * * * *